United States Patent [19]

Ali

[11] Patent Number: 4,623,432
[45] Date of Patent: Nov. 18, 1986

[54] REMOVAL OF BROMINATED ORGANICS FROM ACETIC ACID OBTAINED BY OXIDATION OF LIQUID BUTANE IN PRESENCE OF Co-Br OR Co-Mn-Br SYSTEM CATALYSIS

[75] Inventor: Moinuddin H. Ali, Naperville, Ill.

[73] Assignee: Amoco Corporation, Chicago, Ill.

[21] Appl. No.: 603,079

[22] Filed: Apr. 23, 1984

[51] Int. Cl.[4] .............................................. C07C 51/44
[52] U.S. Cl. ...................................... 203/98; 203/99; 203/DIG. 19; 562/608
[58] Field of Search ................... 203/16, DIG. 19, 88, 203/99, DIG. 6, 98, 94; 562/608, 607

[56] References Cited

U.S. PATENT DOCUMENTS

| | | | |
|---|---|---|---|
| 2,176,500 | 10/1939 | Hyatt | 203/16 |
| 2,275,802 | 3/1942 | Othmer et al. | 203/16 |
| 2,667,502 | 1/1954 | Steitz et al. | 562/608 |
| 2,861,923 | 11/1958 | Elce et al. | 203/63 |
| 3,293,292 | 12/1966 | Olivier et al. | 562/549 |
| 3,438,870 | 4/1969 | Roscher et al. | 203/16 |
| 3,555,083 | 1/1971 | Nakamura et al. | 562/608 |
| 4,111,986 | 9/1978 | Zimmerschied | 562/549 |
| 4,229,261 | 10/1980 | Heck et al. | 203/16 |
| 4,278,503 | 7/1981 | Zeitlin et al. | 562/608 |

Primary Examiner—Wilbur Bascomb
Attorney, Agent, or Firm—Gunar J. Blumberg; William T. McClain; William H. Magidson

[57] ABSTRACT

The recovery of an acetic acid product of low brominated organics content can be made from the liquid effluent from n-butane oxidation with oxygen gas in the presence of an acetic acid solution containing ion of bromine in combination with ions of cobalt or with ions of manganese and cobalt. Such recovery is made not by the use of a series of separate fractionation towers but rather by the use of a single fractionation tower having a top rectification zone, an intermediate stripping zone with a feed inlet at the top thereof and a bottom reboiler zone below the stripping zone wherein the acetic acid product is removed as a vapor product from said stripping zone below said feed inlet but above the reboiler zone.

10 Claims, 1 Drawing Figure

FIG. 1

REMOVAL OF BROMINATED ORGANICS FROM ACETIC ACID OBTAINED BY OXIDATION OF LIQUID BUTANE IN PRESENCE OF Co-Br OR Co-Mn-Br SYSTEM CATALYSIS

FIELD OF INVENTION

This invention relates to the preparation of acetic acid of a bromine content acceptable for use as solvent in the manufacture of aromatic carboxylic acids wherein said solvent is to contain controlled concentrations of bromide ions, or of ions of transition metal oxidation catalysts and/or of gram atoms ratios either of total metals to bromine or of bromine to metals. More specifically this invention pertains to the reaction mixtures from the oxidation of liquid n-butane with oxygen gas in the presence of an acetic acid solution of the catalysts system comprising Co-Mn-Br of U.S. Pat. No. 3,293,292 or the catalyst system Co-Br of U.S. Pat. No. 4,111,986 and the efficient separation of such mixtures into co-products boiling at a temperature lower than the boiling temperature of acetic acid and oxidizable to acetic acid, an acetic acid product fraction suitable as solvent in the manufacture of aromatic carboxylic acids by the oxidation of mono-, di-, or trimethylbenzenes with air, and a residue fraction containing oxidation coproducts and at least metal oxidation catalyst for recycle back to the butane oxidation.

STATE OF THE ART

U.S. Pat. No. 3,293,292 suggests that, following the oxidation of liquid n-butane with oxygen gas at a temperature of from 65° C. up to 232° C. and a gauge pressure of up to 70 kg/cm$^2$, the resulting reaction mixture is distilled to recover as a first fraction, a low boiling ester layer separate from an immiscible water layer and then the acetic acid is recovered as a second fraction contaminated with water. The ester fraction is recovered apparently only for recycle to the butane oxidation to be further oxidized and thus increase the yield of acetic acid. By separating the water-acetic acid mixture as the second fraction there is left a residual acetic acid-contaminant mixture equivalent to that originally charged to the butane oxidation as reaction solvent containing the catalyst components. It is further contemplated by said patent to additionally process the second or acetic acid fraction by adding to it an extraneous material (benzene, toluene, methyl ketone, ethyl ketone, or butyl acetate) which forms an azeotrope with water and subjecting the mixture to distillation for the purpose of removing dissolved water.

U.S. Pat. No. 2,861,923 discloses an improved separation technique whereby an acetic acid fraction and a formic acid fraction of substantially improved quality are recovered from the oxidation at a temperature of 160° to 170° C. and a gauge pressure of from 21 to 42 kg/cm$^2$ of a mixture of paraffinic hydrocarbons (e.g., paraffinic hydrocarbon fraction of boiling range from 15° C. up to 95° C.) which produces a reaction effluent containing (i) volatile non-acidic oxidation products boiling up to 99° C. in the presence of water ("light ends"), (ii) water, (iii) $C_1$ to $C_4$ aliphatic monocarboxylic acids, and (iv) higher boiling residues, including acids having more than four carbon atoms in their molecules. Said improved separation technique comprises the step, after removing light ends (e.g., by flash distillation or flash fractionation with reflux), of separating a mixture containing water and the $C_1$ to $C_4$ aliphatic monocarboxylic acids from the higher boiling residues and then removing by distillation the wet $C_1$ to $C_4$ acid mixture ("subsidiary light ends") which are products of decomposition caused by the residues. Thereafter the water-$C_1$ to $C_4$ aliphatic acid fraction containing at least 8 to 10 weight percent water is in conventional manner, dehydrated by distilling in the presence of a substance (e.g., isopropyl ether) forming an azeotrope with water, followed by distilling the dry acids in the presence of a substance (e.g., toluene) forming an azeotrope with formic acid to remove it as the first monocarboxylic acid product. Then the mixture of $C_2$ to $C_4$ aliphatic monocarboxylic acids are separated into distinct products by fractional distillation.

In said improved separation, no use was suggested for the removed light ends. However, the "subsidiary light ends" (water, ketones and esters) fraction is described as forming two liquid phases: a lower phase mainly water, and an upper organic phase. Discard of the aqueous phase accomplishes part of the dehydration. The organic upper phase is suggested as useful recycle to the oxidation to increase yield of the acid products. Also the patent suggests use of all or part of the lower aqueous phase and/or all or part of the upper organic phase as reflux to the distillative removal of the subsidiary light ends from the mixture of water and $C_1$ to $C_4$ aliphatic acids.

U.S. Pat. No. 3,923,882 is directed to improving the oxidation of liquid $C_3$ to $C_8$ alkanes or alkenes, particularly liquid butane, with molecular oxygen in the presence of a cobalt catalyst to product acetic acid. The improvement comprises replacing methyl ethyl ketone (MEK) or a bromide with ethanol as oxidation promoter. The bromide is replaced because it causes the reaction medium to be corrosive. MEK is replaced because it cannot sustain continuous oxidation more than a few hours. Ethanol does not cause corrosivity and promotes the oxidation of butane to acetic acid more efficiently than MEK promoter.

For recovery of acetic acid from such ethanol promoted cobalt catalyzed oxidation of liquid butane said patent discloses charging the liquid oxidation effluent to a light ends removal column where dissolved unreacted butane and oxygenated compounds boiling lower than acetic acid are distilled off and recycled to the oxidation. The bottoms from the column are charged to a second column for the purpose of removing metal catalyst where 60% of the charged is distilled off to leave a solution of cobalt in acetic acid (propionic acid, butyric acid and butyrolactone also present) as residue for recycle to the oxidation. Said 60% distillate is fed to a drying (third) column from which dry acetic acid is taken as a bottoms product and then subjected to distillative refining (fourth column) to meet commercial specifications for glacial acetic acid.

U.S. Pat. Nos. 3,337,618; 3,337,629; and 3,337,620 are directed to a non-catalytic direct oxidation of propylene with molecular oxygen in a liquid phase comprising fully esterified polyacyl esters of polyols as reaction solvents which are chemically indifferent, thermally stable and high boiling solvents, i.e., high boiling with respect to the volatile oxidation products. Associated with such non-catalytic direct oxidation of propylene is a products separation system whose unique feature is said to comprise in combination two flash decompression zones wherein the sensible heat of the liquid oxidation effluent is used to separate gaseous and vapor acid products from the solvent system and substantially eliminate any solvent in overhead streams. Said combination is further said to minimize the size of downstream (later) distillation and/or fractionation columns and to minimize heat required by them to effect their intended separations. The combination of two flash decompression zones are arranged for series flow therethrough so that after exiting the bottom of the second decompression zone the solvent system contains little (e.g., from 0.05 to 0.2 weight percent) acid products.

All of the foregoing techniques for processing reaction effluents containing acetic acid had as their objectives the recovery of glacial acetic acid (0 to 1 wt.% water) substantially free of aliphatic monocarboxylic acid homologs and certainly substantially free of coproducts oxidatively convertable to acetic acid.

In the more than twenty years since the start of the now dominant commercial manufacture of terephthalic acid, isophthalic acid and trimellitic acid by the oxidation of liquid p-xylene, m-xylene or pseudocumene with air in the presence of catalysis provided by ions of bromine in combination of ions of transition metal oxidation catalysts, (e.g., Co, Ce, Mn or mixtures thereof) high purity acetic acid containing 0 to 3 weight percent water has been the solvent of choice.

However, it has recently been discovered in our laboratories that acetic acid containing other oxygenated aliphatic compounds and having a water content above 3 weight percent, e.g., from 8 to 25 weight percent water, could be successfully used to provide the solvent for such commercial oxidation processes. As sources for such less pure and dry acetic acid only the oxidations of liquid n-butane or commercially available butane containing 95 weight percent n-butane with oxygen gas in liquid acetic acid containing either the Co-Mn-Br or the Co-Br systems of catalysis appeared to be of interest because the known major coproducts of such oxidations were not recognized as undesirable from the standpoint of quality degradation of the commercially produced benzene di- and tricarboxylic acids.

It was first thought that the effluent from such catalytic oxidations of n-butane needed only to be processed to remove the gaseous materials including n-butane and some co-products such as water and organics boiling lower than acetic acid before being suitable as the solvent for the commercial manufacture of the aforementioned benzene di- and tricarboxylic acids. However, for their efficient manufacture at economically compatative costs, the oxidation processes used must have not only controlled concentrations of the transition metals (Co, Mn, or Ce and mixtures thereof), of bromine and of gram atom ratios of bromine to total transition metal catalyst. This meant that not only must the metal catalyst portion of the catalysis for liquid butane oxidation be separated from the liquid oxidation effluent but also most of the sources of bromine had to be removed. The latter was not perceived as difficult until it was found that the liquid oxidation effluent contained brominated coproducts whose relative volatility was close to that of acetic acid. For example the coproduct 3-bromo-2-butanone, have volatilities compared to that of acetic acid of the close relative ratio of 1.17:1.0. Such a volatility relationship indicates that 3-bromo-2-butanone could be separated from acetic acid by fractionation using an inordinately large number of vaporization-separation units, that is, units of packing or trays.

We have now discovered that the liquid oxidation effluent after being substantially decompressed to remove unreacted butane and other gaseous substances together with very low boiling co-products can be successfully processed to remove the brominated coproducts of volatility relatively close to acetic acid as well as catalyst metals by continuous fractionation making use of only a reasonable total number of separation units (units of packing or trays in the stripping and rectification zones having units of separation efficiencies over the temperatures involved of from 48 up to 69% and an overall separation efficiency range for the fractionation system of from 48% up to 67%.

STATEMENT OF INVENTION

The present invention is the removal of brominated organic compounds, mainly 3-bromo-2-butanone, by a one-step hetero-azeotropic distillation of the butane free mixture obtained by the oxidation of n-butane in liquid acetic acid containing catalysis provided by bromide ions in combination with either cobalt ions or cobalt and manganese ions. The bromo-butanone is a by-product of said oxidation.

The 3-bromo-2-butanone impurity comprises from 80 to 95% of the organic bromides present in the oxidation reaction mixture. The relative volatility of 3-bromo-2-butanone with respect to the volatility of acetic acid is substantially unity. Therefore the separation of said bromo-ketone from acetic acid by conventional distillation is sufficiently difficult as not to be commercially feasible.

The concept of the present inventive removal of 3-bromo-2-butanone is based on the following facts. Said brominated ketone is entrained by water in the presence of all the other reaction products. That is the presence of water increases the relative volatility of 3-bromo-2-butanone with respect to the volatility of acetic acid. To provide sufficient water for such entrainment a top vapor temperature of at least 68° C. must be achieved. Also present in the oxidation reaction mixture are acetone, 2-butanone, methyl acetate, ethyl acetate and butyl acetate as low boiling co-products. The acetates can extract said bromo-ketone from the aqueous entrainment environment provided that said environment contains less than 15 weight percent acetic acid. At above 15 weight percent acetic acid the aqueous environment dissolves all the low boiling co-products as well as 3-bromo-2-butanone making the mixture of little use, because of its high water content, as a recycle stream back to n-butane oxidation wherein the acetates, ketones and even 3-bromo-2-butanone can be further oxidized to acetic acid. Such top product of 15 weight percent and above acetic acid content forms at top vapor pressures of 100° C. and above.

By not trying to recover an acetic acid product as an overhead product from the rectification zone of a fractionation system for conducting the present inventive one-step hetero-azeotropic distillation, two additional benefits are obtained. Rather the acetic acid product is taken as a vapor stream below the feed inlet to the stripping zone and above the reboiling zone of the fractionation system. This not only provides an organo-bromide free acetic acid but also acetic acid free of catalyst metals as the first extra benefit. The second benefit is that the residual liquid in the reboiling zone contains not only the catalyst metals but also is high in acetic acid content and sufficiently low in water content to permit its reuse as acetic acid source and source of metal catalyst component of the n-butane oxidation catalysis.

When the present inventive hetero-azeotropic fractional distillation is conducted to provide a top fraction comprising an aqueous product containing less than 15 weight percent acetic acid, the top fraction vapors when cooled to below the boiling points of the components, the resulting liquid condensate upon settling forms two immiscible phases: a top low boiling organic product and an aqueous product.

Figure 1:
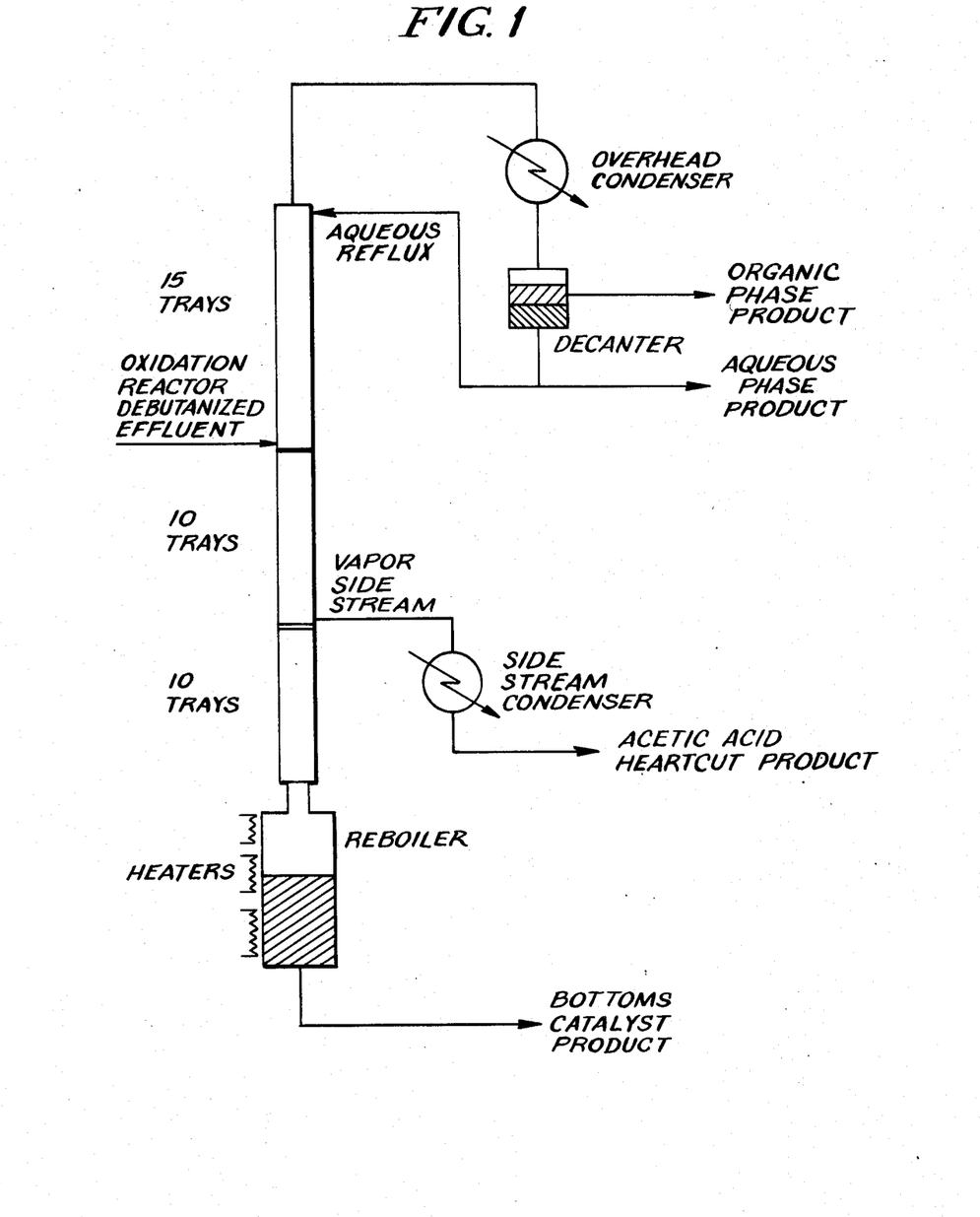
FIGURE 1 is a schematic flow diagram of the present invention.

The present inventive hetero-azeotropic fractional distillation can be practiced by one of the several modes of operation to follow.

In one mode, the aqueous product is recycled to the top of the rectification zone as reflux liquid and the net buildup of the aqueous product is removed. The organic product, comprised mainly of the acetates, is rich in 3-bromo-butanone and is recycled to n-butane oxidation. The bromide content of the acetic acid vapor product (removed from below the feed inlet to the stripping zone) by this mode can be as low as 0.003 weight percent.

A modification of the first mode of operation comprises total reflux of the aqueous product. This maximizes removal of 3-bromo-2-butanone by the organic product (99.5% or more of the organo-bromides are removed) but water is removed in the acetic acid product.

A second mode of operation involves recycle of part of the aqueous product to the stripping zone below the point of entrance thereto of feed but above the point of exit of the vaporous acetic acid product. This facilitates enhanced 3-bromo-2-butanone recovery in the organic product and lowers the 3-bromo-2-butanone content of the acetic acid product to as low as 0.002 to 0.001 weight percent.

A third mode of operation, which decreases the energy requirements for separating water from acetic acid makes use of the low-boiling organic product containing the acetates as reflux liquid recycled to the rectification zone of the fractionation system near the feed entry thereto. This enhances water removal because the organic product forms a low boiling temperature azeotrope with water. The aqueous product can also be recycled but, most advantageously, to a point below the feed entrance but above the point whereat the acetic acid vapor product is withdrawn. Part of all of the aqueous product, which is quite low in 3-bromo-2-butanone, can also be added back to the column below the feed entrance and even below the acetic acid vapor product drawoff. Such use of the aqueous product enhances somewhat the stripping of 3-bromo-2-butanone but does cause some dilution of the acetic acid product which can be tolerated when it is desired to further and separately concentrate the acetic acid product. For example, by distillation including azeotropic distillation employing an extraneous (outside added) azeotropic agent for water removal.

A fourth mode of operation utilizes part of the low-boiling organic product as reflux liquid added above the acetic acid vapor drawoff but below the feed entrance to improve azeotropic removal of water and thus reduce energy requirements. The aqueous phase is then totally recycled as reflux liquid to the upper part of the rectification zone. This provides better removal of 3-bromo-2-butanone than the third mode of operation does and results in an acetic acid product containing between 0.005 and 0.01 weight percent of said bromo butanone.

The fifth mode of operation is especially useful in the manufacture of glacial acetic acid by splitting the low-boiling organic product into a major portion and a minor portion. The latter is recycled to the top of the rectification zone as its source of reflux. The major portion is added to the stripping zone either with the feed or at a point between its entrance and the withdrawal of the acetic acid vapor product. In this operation none of the aqueous product is recycled to the fractionation system. The acetic acid vapor product withdrawn can contain as little as 0.5 weight percent water or can have from 3 to 5 weight percent water. The low water content product has a 3-bromo-2-butanone content from 0.005 to 0.02 weight percent. The 3 to 5 weight percent water content acetic acid product will have a somewhat higher, 0.02 to 0.05 weight percent, content of 3-bromo-2-butanone.

The feed to the hetero-azeotropic fractional distillation of this invention is the debutanized portion of the reaction mixture remaining after removal of unreacted butane and $CO_2$ from the liquid effluent produced by the oxidation of liquid n-butane with oxygen gas in the presence of an acetic acid solution of a system of catalysis provided by ions of cobalt and bromine or by ions of cobalt, manganese and bromine at a temperature of from 120° C. up to 235° C. and at a gauge pressure of from 28 up to 210 $kg/cm^2$. Said debutanization of the reaction mixture occurs upon decompressing the oxidation reaction mixture to a gauge pressure of from 3.5 to 21 $kg/cm^2$ while maintaining the liquid at a temperature in the range of from 85° C. up to 180° C. The debutanized portion of the n-butane oxidation reaction mixture will have somewhat similar compositions even though the systems of catalysis do differ. For example, such debutanized portions will have in addition to the metals and inorganic bromides, the general typical compositions whose components are shown in weight percent in TABLE I.

TABLE I

Typical Compositions of Debutanized Reaction Portion of Mixtures from the Butane Oxidation in the Presence of Different Systems of Catalysis

| Composition Component | Catalysis | |
|---|---|---|
| | Co-Br | Co-Mn-Br |
| Acetic Acid | 67 to 77% | 65 to 72% |
| Water | 12 to 21% | 18 to 20% |
| Light By-Products | 5 to 6% | 2.4 to 3.5% |
| Heavy By-Products | 3 to 5% | 4.8 to 7.3% |
| 3-bromo-2-butanone | 0.5 to 0.9% | 0.2 to 0.35% |

The separation of organic bromides is accomplished by increasing their relative volatility with respect to acetic acid during the fractional distillation of said debutanized portion of the oxidation reaction mixture. Such increase in relative volatility of the bromine-containing organic compounds is effected not by the use of an extraneously added azeotrope forming material. Rather the relative volatility increase is effected by enhancing the azeotrope formation between water and the organic bromides permitting them to be removed as solutes in the organic portion of the top or first fraction. Quite unexpectedly, said azeotrope formation can be enhanced by recycling as reflux either the organic phase or the water phase portion of a two phase forming top fraction.

The same fractional distillation permits rejection of the catalyst metals in the bottom or residual fraction and taking of an acetic acid concentrate containing as little as 0.5 weight percent water as an intermediate or second fraction.

All of foregoing can be accomplished, provided certain critical operations are met, in a single fractional distillation system comprising a rectification zone, a feed inlet below said zone, a stripper zone below the feed inlet, an acetic acid concentrate removal below the feed inlet, and a reboiler zone below the stripper zone to supply thereto heat and vapors to effect acetic acid concentration in the stripper zone. The critical operating conditions are those which provide a top vapor mixture which upon cooling below its components boiling point forms two immiscible liquid layers upon settling; an upper organic product and a lower aqueous product, either of which, as before stated, when recycled to provide reflux for the fractionation system enhance removal of the bromo-organic impurities.

The formation of said top vapors providing on cooling the two products depends, we have found, upon the operating vapor temperature at the top of the rectification zone and not the temperature of the feed.

In general, such conditions are satisfied for the fractional distillation system operated at substantially atmospheric pressure (0 gauge pressure) at the top and acetic acid product fractions recoveries when the vapor temperature at the top of the rectification zone is above 68° but does not exceed 100° C. Operating the reboiler zone at a temperature of from 120° C. up to 135° C. will provide said top vapor temperatures.

Such a fractional distillation system can have its rectification and stripper zones as part of a single column having separation units with separating efficiencies between 48 and 57% and comprising units filled with various packings, sieve tray units or units having liquid flooded trays having bubble caps for release of upward moving vapors into the liquid on the tray and down flow tubes for moving the liquid from one tray to a lower tray. For example, a single column can be used having thirty-five (35) trays of 48 to 57% separation efficiency (48 to 50% efficiency in the stripper zone and 50 to 57% efficiency in the rectification zone) where the acetic acid feed (debutanized oxidation effluent) enters on the tray fifteenth from the top and the acetic acid product (intermediate acetic acid concentrate fraction) is withdrawn from the tray ninth or tenth down from the feed inlet, preferably withdrawn as vapor from between said ninth and tenth tray down from the feed inlet. Such a column has a fourteen (14) tray rectification zone and a twenty (20) tray stripper zone respectively above and below the feed entrance tray.

By withdrawing the acetic acid concentrate product or intermediate fraction as a vapor product, according to the preferred operation of the fractionation system, such intermediate fraction does not contain any of the catalyst metals. Said metals then continue down the column with high boiling liquid and flow into the reboiler zone from which they are withdrawn dissolved in said liquid and can be recycled back to the oxidation of liquid n-butane.

There are operating conditions associated with and important for the recycle of the aqueous layer or the organic layer portion of the top fraction condensate as liquid reflux to the retification zone. Such conditions are ratio of total modes of components in the top fraction to total modes in the feed. For recycle of the aqueous phase said ratio should be from 2.4:1 to 4.0:1.0 and for recycle of the organic phase the ratio should be from 0.4:1 to 0.8:1.0.

Also of importance is the operating temperature of cooling the top vapor fraction. When the aqueous phase is being recycled as reflux to the rectification zone said cooling need be in the range of from 20° C. to 32° C. For the recycle of the organic phase as reflux to the rectification zone such cooling is in the range of from 16° C. up to 19° C. However, the aqueous phase is heated to a temperature of 80° to 85° C. and the organic phase is heated to a temperature of from 45° up to 50° C. before entering the rectification zone as its reflux liquid.

In the absence of the foregoing knowledge and operating according to the state of the art extant before such knowledge various results were possible from the fractional distillation of the n-butane-free portion of the oxidation effluent. Where the object of such fractional distillation was to maximize acetic acid production as glacial acetic acid then, as described before, one or more azeotrope forming agents were used in a multicolumn fractional distillation system. In such situation no provision was needed to recover oxidation catalyst components as solutes in solvent used in the oxidation. Upon the advent of the oxidation process of the U.S. Pat. No. 3,293,292 there became desirable for the first time the recovery of the metal components of catalysis as solutes in acetic acid, the preferred oxidation reaction solvent.

We further discovered, since the available state of the art did not present evidence of less successful distillative acetic acid recovery processes, why single column fractional distillation systems for acetic acid recovery were not suggested as feasible routes.

For example, when using one of the n-butane free compositions of TABLE I as the feed to a fractional distillation system operated at ambient atmospheric pressure (i.e., 0 gauge pressure). Such a system comprises a single column of 20 sieve trays having a separation efficiency of 48 to 57% with the feed composition entering on the fifth tray from the bottom (fifteenth from the top) tray. The top fraction upon cooling the components of the vapor mixture below their boiling and settling the resulting liquid did not form two immiscible liquid layers when maximizing removal of acetic acid product of low, 5 weight percent or below, water content. Such two immiscible layers did not form even when taking such product as a vapor product above the reboiler as suggested by U.S. Pat. No. 3,490,997. To so take the acetic acid as a vapor product assures that the product does not contain dissolved metals. However, so taking the product does not limit its halide content unless an alkali metal is used as said patent also suggest.

As we also found, said top fraction did not form two immiscible liquids upon cooling the vapors below their boiling temperature and settling the condensate when said fraction is permitted to contain at least fifteen weight percent acetic acid. At such high acetic acid concentration the other organics (e.g., methyl, ethyl, and butyl acetates) are solubilized in the water by the acetic acid.

In contrast to the foregoing the n-butane-free compositions of TABLE I can be converted to catalyst metal-free, low bromine content, bromide concentration from 1500 down to 30 ppm (weight parts per million weight parts of product) and also recover an acetic acid product not exceeding four weight percent water by the practice of the present inventive fractional distillation method. For example, the ambient atmospheric fractional distillation is conducted in a single column containing a total of 35 sieve trays each of which have a separation efficiency of 48 to 57% with the feed entering on the fifteenth tray down from the top tray and with the acetic acid vapor product being taken from the vapor space between the ninth and tenth tray below the feed tray (i.e., between the twenty-fourth and twenty-fifth tray from the top tray). The top fraction after cooling its vapor composition below the boiling point of its components and settling the resulting condensate forms two immiscible liquid layers whose total acetic acid content is below fifteen weight percent. Hence the acetic acid was dissolved in the aqueous layer which also contained most of the bromine-containing compounds. The organic layer containing ketones, alcohols, and methyl to butyl acetates or the aqueous layer containing acetic acid and the bromides after the separation of the layers from each other, can be recycled to the upper portion of the column as reflux thereto.

However, by employing the organic layer as an azeotroping agent with water rather than only as reflux liquid recycled to the upper portion of the distillation column, a low (3 to 5 wt%) water content acetic acid product can be withdrawn as a vapor product below the feed entrance to the column. None of the aqueous layer is recycled to the column. In such option a small portion of the organic layer is recycled to the top of the column and a large portion of the organic layer is recycled to a lower point, that is from the feed entrance to just above the withdrawal of vapor product from the column. Such a fractionation is conducted with a feed entering at a temperature of from 90° to 100° C., a top column temperature of between 75° and 100° C. and a pressure at the top of the column of 0 kg/cm² gauge pressure.

ILLUSTRATIONS OF SPECIFIC MODES OF OPERATION

The following examples illustrate three of the different modes of operation of the present inventive heterofractionation previously discussed. Also, with respect to the quality of the acetic acid product obtained, they represent the best mode of operation currently contemplated.

In all of the twelve illustrtive modes of practice of the present hetero-azeotropic fractional distillation the same apparatus configuration is used. The total fractionation column (stripping zone plus rectification zone) comprises 35 sieve trays having an overall column efficiency of 55%. The feed (debutanized oxidation reaction effluent) is introduced on the fifteenth tray from the top. Acetic acid vapor product is withdrawn from the vapor space between the twenty-fifth and twenty-sixth trays from the top. The bottom of the column is attached to a heatable reboiler to supply heat to the contents thereof and vaporize a portion of the reboiler's contents as a supply of hot vapors to the stripping zone. The acetic acid vapor product exits the column (exit is between plate 25 and 26) through a vapor transfer conduit connecting the column with an acetic acid product cooler operated at a temperature below the acetic acid product boiling point so that a liquid product can be collected. Vapors exiting from the rectification zone at the top of the column above the first tray are transferred by vapor transfer conduit to a cooler operated at a temperature below the boiling point of the vapor mixture. The top vapor condensate is collected in a decanter from which a top organic (mainly acetate) product can be withdrawn and, if desired, recycled in whole or in part to the column and from which an aqueous product can be withdrawn, and, if desired, recycled in whole or in part to the column.

The use of the aqueous product as reflux to the hetero-azeotropic fractional distillation was made to the top tray of the rectification zone (tray 1 of the column). The use of the organic product as reflux to said fractional distillation was made to one of the trays between the feed entrance (tray 16 from top) and just above acetic acid vapor product exit from the column; i.e., to tray 25 from the top. It was more advantageous to add the organic product as reflux liquid to tray 16 from the top.

EXAMPLE 1

In this fractional distillation the organic product is recycled to the stripping zone of the column and enters on the feed tray (i.e., 16 from top).

The operating conditions are:
Feed Rate: 25.6 gram per minute
Acetic Acid Product: 16.65 gram per minute
Organic Product: 1.44 gram per minute
Aqueous Product: 1.77 gram per minute
Reboiler Product: 5.75 gram per minute
Reboiler Temperature: 122° C.
Top Vapor Temperature: 82° C.
Feed Tray Temperature: 102.5° C.
Acetic Acid Vapor Product Temperature: 106.7°
Molar Ratio Organic Product to Feed: 0.26:1.0
Molar Ratio Acetic Acid Product to Feed: 0.66:1.0
Organic Product Reflux to Feed Ratio: 0.51:1.0
The feed to and fractions from the process:

| Component Weight Percent | Feed | Products Acetic Acid | Organic | Aqueous | Reboiler Liquid |
|---|---|---|---|---|---|
| Methyl Acetate | 2.64 | 0 | 20.39 | 4.81 | 0 |
| Ethyl Acetate | 1.47 | 0 | 17.49 | 1.88 | 0 |
| 2-Butanone | 1.19 | 0 | 14.59 | 3.47 | 0 |
| Light By-Products | 1.80 | 0.73 | 9.74 | 1.77 | 0.41 |
| 3-Bromo-2-Butanone | 0.51 | 0.006 | 13.26 | 0.74 | 0 |
| Acetic Acid | 68.1 | 84.1 | 9.49 | 5.97 | 85.6 |
| Water | 21.4 | 13.9 | 11.05 | 79.4 | 0.30 |
| Propionic Acid | 1.29 | 1.09 | 1.4 | 0.67 | 6.35 |
| Heavy By-Products | 1.31 | 0.1 | 2.3 | 0.30 | 8.15 |
| Ionic Bromine | 0.21 | 0 | 0 | 0 | 1.78 |
| Cobalt | 0.28 | 0 | 0 | 0 | 2.15 |
| Acetic Acid Recovered: 73% | | | | | |

EXAMPLE 2

In this example a portion of the organic product is recycled as reflux to the top tray.
The operating conditions are:
Feed Rate: 25.71 grams per minute
Acetic Acid Product: 16.43 grams per minute
Organic Product: 0.43 grams per minute
Aqueous Product: 4.08 grams per minute
Reboiler Product: 5.46 grams per minute
Reboiler Temperature: 122° C.
Top Vapor Temperature: 86° C.
Feed Tray Temperature: 102.8° C.
Acetic Acid Product Temperature: 102° C.
Molar Ratio Organic Product to Feed: 0.011:1.0
Molar Ratio Acetic Acid Product to Feed: 0.604:1.0
Organic Product Reflux to Feed: 0.713:1.0
The feed to and fractions from the process:

| Component Weight Percent | Feed | Products Acetic Acid | Organic | Aqueous | Reboiler |
|---|---|---|---|---|---|
| Acetone | 0.37 | 0 | 0.38 | 0 | 0 |
| Methyl Acetate | 2.52 | 0 | 1.45 | 1.14 | 0 |
| Ethyl Acetate | 1.59 | 0 | 26.90 | 5.38 | 0 |
| 2-Butanone | 1.32 | 0 | 26.34 | 3.07 | 0 |
| s-Butyl Acetate | 0.34 | 0 | 18.92 | 4.59 | 0 |
| n-Butyl Acetate | 0.06 | 0 | 7.34 | 0.23 | 0 |
| 3-Bromo-2-Butanone | 0.62 | 0 | 0.54 | 0.01 | .004 |
| Formic Acid | 0.65 | 0.88 | 4.91 | 0.31 | 0.51 |
| Water | 22.19 | 18.96 | 0.44 | 0.60 | 0.77 |
| Acetic Acid | 65.92 | 79.15 | 9.71 | 76.33 | 90.03 |
| Propionic Acid | 1.68 | 0.90 | 1.44 | 7.49 | 3.09 |
| Isobutyric Acid | 0 | 0 | 0.23 | 0.12 | 0 |
| n-Butyric Acid | 0.58 | 0.11 | 0 | 0 | 1.26 |
| Heavy By-Products | 1.30 | 0 | 0.05 | 0.01 | 1.33 |
| Ionic Bromine | 0.39 | 0 | 1.31 | 0.71 | 1.53 |
| Cobalt | 0.29 | 0 | 0 | 0 | 1.44 |
| Acetic Acid Recovered: 76.7% | | | | | |

EXAMPLE 3

In this example part of the organic product is recycled to the top tray.

The operating conditions are:
Feed Rate: 32.81 grams per minute
Acetic Acid Product: 24.92 grams per minute
Organic Product: 1.16 grams per minute
Aqueous Product: 4.99 grams per minute
Reboiler Product: 3.19 grams per minute
Reboiler Temperature: 126.7° C.
Top Vapor Temperature: 85.6° C.
Feed Tray Temperature: 103° C.
Acetic Acid Product Temperature: 102° C.
Molar Ratio Organic Product to Feed: 0.021:1.0
Molar Ratio Acetic Acid Product to Feed: 0.662:1.0
Molar Ratio Organic Product Reflux to Feed: 0.514:1.0

The feed to and fractions from the process:

| Component Weight Percent | Feed | Products Acetic Acid | Organic | Aqueous | Reboiler |
|---|---|---|---|---|---|
| Acetone | 0.19 | 0 | 1.03 | 1.29 | 0 |
| Methyl Acetate | 2.25 | 0 | 30.1 | 8.17 | 0 |
| Ethyl Acetate | 1.30 | 0 | 23.09 | 3.22 | 0 |
| 2-Butanone | 1.16 | 0.01 | 15.88 | 4.55 | 0 |
| s-Butyl Acetate | 0.29 | 0 | 7.56 | 0.32 | 0 |
| n-Butyl Acetate | 0 | 0 | 0.10 | 0.11 | 0 |
| 3-Bromo-2-Butanone | 0.54 | 0.02 | 9.81 | 0.54 | 0.12 |
| Formic Acid | 0.61 | 0.71 | 0.25 | 0.59 | 0.69 |
| Water | 21.5 | 14.82 | 8.56 | 74.98 | 0.08 |
| Acetic Acid | 68.87 | 83.24 | 1.0 | 5.07 | 76.65 |
| Propionic Acid | 1.32 | 1.04 | 0.21 | 0.08 | 4.96 |
| n-Butyric Acid | 0.46 | 0.11 | 0.03 | 0.01 | 3.30 |
| Heavy By-Products | 0.73 | 0.03 | 2.32 | 1.07 | 6.40 |
| Ionic Bromine | 0.40 | 0 | 0 | 0 | 4.69 |
| Cobalt | 0.29 | 0 | 0 | 0 | 3.10 |
| Acetic Acid Recovered: 91.8% | | | | | |

EXAMPLE 4

In this example part of the organic product is recycled to the top tray.

The operating conditions are:
Feed Rate: 14 grams per minute
Acetic Acid Product: 8.15 grams per minute
Organic Product: 0.58 grams per minute
Aqueous Product: 2.22 grams per minute
Reboiler Product: 2.50 grams per minute
Reboiler Temperature: 123° C.
Top Vapor Temperature: 87.8° C.
Feed Tray Temperature: 103.6° C.
Molar Ratio Organic Product to Feed: 0.28:1.0
Molar Ratio Acetic Acid Product to Feed: 0.512:1.0
Molar Ratio Organic Reflux to Feed: 0.74:1.0

The feed to and fractions from the process:

| Component Weight Percent | Feed | Products Acetic Acid | Organic | Aqueous | Reboiler |
|---|---|---|---|---|---|
| Acetone | 0.18 | 0 | 1.55 | 1.41 | 0 |
| Methyl Acetate | 1.99 | 0 | 19.43 | 5.10 | 0 |
| Ethyl Acetate | 1.13 | 0 | 19.43 | 3.03 | 0 |
| 2-Butanone | 1.31 | 0 | 17.13 | 5.30 | 0 |
| s-Butyl Acetate | 0.31 | 0 | 6.62 | 0.27 | 0 |
| n-Butyl Acetate | 0.04 | 0 | 0.76 | 0.18 | 0 |
| 3-Bromo-2-Butanone | 0.74 | 0 | 9.16 | 0.39 | 0 |
| Formic Acid | 0.56 | 0.89 | 1.04 | 0.42 | 0.27 |
| Water | 21.21 | 7.93 | 12.74 | 76.31 | 0.04 |
| Acetic Acid | 68.23 | 90.0 | 9.30 | 6.07 | 85.13 |
| Propionic Acid | 1.90 | 0.94 | 0.32 | 0.13 | 5.77 |
| n-Butyric Acid | 0.71 | 0.21 | 0.07 | 0.02 | 2.80 |
| Heavy By-Products | 1.11 | 0.01 | 2.23 | 1.29 | 3.28 |
| Ionic Bromine | 0.22 | 0.02 | 0.04 | 0.07 | 1.30 |
| Cobalt | 0.29 | 0 | 0.01 | 0.01 | 1.41 |
| Acetic Acid Recovered: 76.8% | | | | | |

EXAMPLE 5

In this example part of the aqueous product is recycled to the top tray.

The operating conditions are:
Feed Rate: 12.8 grams
Acetic Acid Product: 8.8 grams
Organic Product: 0.72 grams
Aqueous Product: 1.82 grams
Reboiler Product: 1.52 grams
Reboiler Temperature: 125.6° C.
Top Vapor Temperature: 98.3° C.
Feed Tray Temperature: 101.7° C.
Acetic Acid Product Temperature: 107.8° C.
Molar Ratio Aqueous Product Reflux to Feed: 1.82:1.0
Molar Ratio Acetic Acid Product to Feed: 0.685:1.0

The feed to and fractions from the process:

| Component Weight Percent | Feed | Products Acetic Acid | Organic | Aqueous | Reboiler |
|---|---|---|---|---|---|
| Acetone | 0.16 | 0 | 1.0 | 1.0 | 0 |
| Methyl Acetate | 1.64 | 0 | 20.39 | 4.81 | 0 |
| Ethyl Acetate | 0.94 | 0 | 17.49 | 1.88 | 0 |
| 2-Butanone | 1.11 | 0 | 14.59 | 3.47 | 0 |
| s-Butyl Acetate | 0.27 | 0 | 7.5 | 0.3 | 0 |
| n-Butyl Acetate | 0.04 | 0 | 0.15 | 0.1 | 0 |
| 3-Bromo-2-Butanone | 0.79 | 0.006 | 13.26 | 0.74 | 0 |
| Formic Acid | 0.49 | 0.9 | 1.0 | 0.4 | 0.3 |
| Water | 21.5 | 13.9 | 11.05 | 79.4 | 0.30 |
| Acetic Acid | 69.1 | 84.1 | 9.49 | 5.97 | 85.6 |
| Propionic Acid | 1.88 | 1.09 | 1.40 | 0.67 | 6.35 |
| n-Butyric Acid | 0.63 | 0.095 | 0.7 | 0.005 | 3.19 |
| Heavy By-Products | 0.98 | 0.005 | 1.6 | 0.295 | 4.96 |
| Ionic Bromine | 0.21 | 0 | 0 | 0 | 1.78 |
| Cobalt | 0.29 | 0 | 0 | 0 | 2.15 |
| Acetic Acid Recovered: 83.7% | | | | | |

EXAMPLE 6

In this example all of the aqueous product is recycled to the top tray.

The operating conditions are:

Feed Rate: 31.5 grams per minute
Acetic Acid Product: 22.7 grams per minute
Organic Product: 2.6 grams per minute
Aqueous Product: 0 (total reflux of this product)
Reboiler Product: 6.2 grams per minute
Reboiler Temperature: 122° C.
Top Vapor Temperature: 97.2° C.
Feed Tray Temperature: 102.8° C.
Acetic Acid Product Temperature: 108.3° C.
Weight Ratio Aqueous Reflux to Feed: 0.77:1.0
Weight Ratio Acetic Acid Product to Feed: 0.72:1.0
The feed to and fractions from the process:

| Component Weight Percent | Feed | Products Acetic Acid | Organic | Reboiler |
|---|---|---|---|---|
| Methyl Acetate | 1.89 | 0 | 24.3 | 0 |
| Ethyl Acetate | 1.34 | 0 | 18.8 | 0 |
| 2-Butanone | 1.09 | 0.013 | 15.0 | 0 |
| s-Butyl Acetate | 0.27 | | | |
| 3-Bromo-2-Butanone | 0.62 | 0.01 | 8.72 | 0.05 |
| Formic Acid | | | | |
| Water | 19.6 | 26.6 | 13.9 | 0.093 |
| Acetic Acid | 71.6 | 71.9 | 6.87 | 89.1 |
| Propionic Acid | 1.23 | 0.67 | 0.69 | 4.05 |
| Ionic Bromine | 0.35 | 0 | 0 | 1.92 |
| Cobalt | 0.27 | 0 | 0 | 2.16 |

Acetic Acid Recovered: 72.4%

EXAMPLE 7

In this example part of the aqueous product is recycled to the top tray.
The operating conditions are:
Feed Rate: 21.1 grams per minute
Acetic Acid Product: 12.41 grams per minute
Organic Product: 0.44 grams per minute
Aqueous Product: 5.56 grams per minute
Reboiler Product: 2.44 grams per minute
Reboiler Temperature: 126.7° C.
Top Vapor Temperature: 98.9° C.
Feed Tray Temperature: 103.9° C.
Acetic Acid Product Temperature: 91° C.
Molar Ratio Aqueous Product Reflux to Feed: 1.93:1.0
Molar Ratio Acetic Acid Product to Feed: 0.465:1.0
The feed to and fractions from the process:

| Component Weight Percent | Feed | Products Acetic Acid | Organic | Aqueous | Reboiler |
|---|---|---|---|---|---|
| Acetone | 0.30 | 0 | 1.11 | 1.0 | 0 |
| Methyl Acetate | 1.97 | 0 | 19.2 | 4.8 | 0 |
| Ethyl Acetate | 1.13 | 0 | 22.29 | 2.76 | 0 |
| 2-Butanone | 1.0 | 0 | 16.60 | 3.37 | 0 |
| s-Butyl Acetate | 0.23 | 0 | 5.72 | 0.30 | 0 |
| n-Butyl Acetate | 0.03 | 0 | 0.92 | 0.10 | 0 |
| 3-Bromo-2-Butanone | 0.41 | 0 | 8.38 | 0.82 | 0.06 |
| Formic Acid | 0.64 | 1.10 | 0.36 | 0.33 | 0.37 |
| Water | 22.78 | 7.63 | 11.16 | 72.85 | 0.08 |
| Acetic Acid | 67.95 | 90.16 | 6.21 | 4.46 | 77.18 |
| Propionic Acid | 1.22 | 0.93 | 1.40 | 0.44 | 6.68 |
| n-Butyric Acid | 0.53 | 0.11 | 0.85 | 0.10 | 5.47 |
| Heavy By-Products | 0.97 | 0 | 4.59 | 1.21 | 4.91 |
| Ionic Bromine | 0.40 | 0 | 0.31 | 0.03 | 3.07 |
| Cobalt | 0.28 | 0 | 0.05 | 0.01 | 2.36 |

Acetic Acid Recovered: 78%

EXAMPLE 8

In this example part of the aqueous product is recycled to the top tray.
The operating conditions are:
Feed Rate: 21.1 grams per minute
Acetic Acid Product: 11.62 grams
Organic Product: 0.37 grams
Aqueous Product: 4.99 grams
Reboiler Product: 3.46 grams
Reboiler Temperature: 124.7° C.
Top Vapor Temperature: 98.9° C.
Feed Tray Temperature: 103.6° C.
Molar Ratio Aqueous Product Reflux to Feed: 2.018:1.0
Molar Ratio Acetic Acid Product to Feed: 0.451:1.0
The feed to and fractions from the process:

| Component Weight Percent | Feed | Products Acetic Acid | Organic | Aqueous | Reboiler |
|---|---|---|---|---|---|
| Acetone | 0.31 | 0 | 1.22 | 1.10 | 0 |
| Methyl Acetate | 2.0 | 0 | 12.06 | 5.19 | 0 |
| Ethyl Acetate | 1.16 | 0 | 21.23 | 2.75 | 0 |
| 2-Butanone | 1.03 | 0 | 13.5 | 3.25 | 0 |
| s-Butyl Acetate | 0.25 | 0 | 8.80 | 0.31 | 0 |
| n-Butyl Acetate | 0.04 | 0 | 1.03 | 0.42 | 0 |
| 3-Bromo-2-Butanone | 0.41 | 0 | 10.12 | 0.77 | 0.04 |
| Formic Acid | 0.68 | 1.12 | 0.55 | 0.27 | 0.37 |
| Water | 20.65 | 6.70 | 11.83 | 72.15 | 0.04 |
| Acetic Acid | 69.98 | 91.39 | 12.38 | 12.00 | 85.29 |
| Propionic Acid | 1.21 | 0.64 | 0.68 | 0.35 | 3.99 |
| n-Butyric Acid | 0.52 | 0.07 | 0.35 | 0.07 | 2.40 |
| Heavy By-Products | 0.91 | 0 | 5.01 | 1.35 | 3.64 |
| Ionic Bromine | 0.40 | 0 | 0.03 | 0.03 | 2.52 |
| Cobalt | 0.27 | 0 | 0.05 | 0 | 1.70 |

Acetic Acid Recovered: 71.9%

EXAMPLE 9

In this example part of the aqueous product is recycled to the feed tray.
The operating conditions are:
Feed Rate: 17.0 grams per minute
Acetic Acid Product: 10.2 grams per minute
Organic Product: 0.70 grams per minute
Aqueous Product: 3.73 grams per minute
Reboiler Product: 1.42 grams per minute
Reboiler Temperature: 136.4° C.
Top Vapor Temperature: 98.9° C.
Feed Tray Temperature: 102.8° C.
Molar Ratio Aqueous Product Reflux to Feed: 2.735:1.0
Molar Ratio Acetic Acid Product to Feed: 0.489:1.0
The feed to and fractions from the process:

| Component Weight Percent | Feed | Products Acetic Acid | Organic | Aqueous | Reboiler |
|---|---|---|---|---|---|
| Acetone | 0.23 | 0 | 0.97 | 0.86 | 0 |
| Methyl Acetate | 1.87 | 0 | 1.04 | 14.35 | 0 |
| Ethyl Acetate | 1.65 | 0 | 22.75 | 2.89 | 0 |
| 2-Butanone | 1.68 | 0 | 16.43 | 4.22 | 0 |
| s-Butyl Acetate | 0.22 | 0 | 0.08 | 2.53 | 0 |
| n-Butyl Acetate | 0.05 | 0.10 | 0.86 | 0.11 | 0 |
| 3-Bromo-2-Butanone | 0.46 | 0.02 | 9.09 | 0.62 | 0 |
| Formic Acid | 0.65 | 0.98 | 0.65 | 0.36 | 0.42 |
| Water | 20.99 | 5.43 | 11.74 | 75.76 | 0.10 |
| Acetic Acid | 66.7 | 91.21 | 6.75 | 8.42 | 60.83 |
| Propionic Acid | 2.47 | 1.97 | 1.70 | 0.80 | 11.90 |
| n-Butyric Acid | 1.3 | 0.25 | 1.18 | 0.23 | 11.1 |

-continued

| Component Weight Percent | Feed | Products | | | |
|---|---|---|---|---|---|
| | | Acetic Acid | Organic | Aqueous | Reboiler |
| Heavy By-Products | 0.91 | 0 | 2.87 | 1.40 | 7.98 |
| Ionic Bromine | 0.31 | 0 | 0.01 | 0.00 | 4.38 |
| Cobalt | 0.25 | 0 | 0.06 | 0.01 | 3.77 |
| Acetic Acid Recovered: 82% | | | | | |

EXAMPLE 10

In this example part of the aqueous product is recycled to the feed tray.

The operating conditions are:
Feed Rate: 17.95 grams per minute
Acetic Acid Product: 10.79 grams per minute
Organic Product: 0.80 grams per minute
Aqueous Product: 4.20 grams per minute
Reboiler Product: 1.57 grams per minute
Reboiler Temperature: 132.8° C.
Top Vapor Temperature: 98.9° C.
Feed Tray Temperature: 103.3° C.
Molar Ratio Aqueous Product Reflux to Feed: 2.469:1.0
Molar Ratio Acetic Acid Product to Feed: 0.465:1.0
The feed to and fractions from the process:

| Component Weight Percent | Feed | Products | | | |
|---|---|---|---|---|---|
| | | Acetic Acid | Organic | Aqueous | Reboiler |
| Acetone | 0.26 | 0 | 0.82 | 0.34 | 0 |
| Methyl Acetate | 1.80 | 0 | 25.74 | 4.48 | 0 |
| Ethyl Acetate | 1.62 | 0 | 21.95 | 3.24 | 0 |
| 2-Butanone | 1.64 | 0 | 15.86 | 4.52 | 0 |
| s-Butyl Acetate | 0.24 | 0 | 5.34 | 0.23 | 0 |
| n-Butyl Acetate | 0.04 | 0 | 0.90 | 0.42 | 0 |
| 3-Bromo-2-Butanone | 0.48 | 0 | 8.79 | 0.65 | 0 |
| Formic Acid | 0.78 | 1.0 | 0.20 | 0.60 | 0.03 |
| Water | 21.81 | 4.68 | 12.29 | 73.64 | 0.01 |
| Acetic Acid | 65.72 | 92.09 | 1.75 | 9.21 | 63.78 |
| Propionic Acid | 2.58 | 1.97 | 1.29 | 0.62 | 13.0 |
| n-Butyric Acid | 1.30 | 0.22 | 0.75 | 0.16 | 8.10 |
| Heavy By-Products | 1.07 | 0 | 3.47 | 1.35 | 7.14 |
| Ionic Bromine | 0.32 | 0 | 0.01 | 0.02 | 2.89 |
| Cobalt | 0.26 | 0 | 0.05 | 0.01 | 2.53 |
| Acetic Acid Recovered: 84.2% | | | | | |

EXAMPLE 11

In this example part of the aqueous product is recycled to the feed tray.

The operating conditions are:
Feed Rate: 17.99 grams per minute
Acetic Acid Product: 10.91 grams per minute
Organic Product: 0.68
Aqueous Product: 4.38
Reboiler Product: 1.58
Reboiler Temperature: 132.8° C.
Top Vapor Temperature: 98.9° C.
Feed Tray Temperature: 103.3° C.
Molar Ratio Aqueous Product to Feed: 2.457:1.0
Molar Ratio Acetic Acid Product to Feed: 0.46:10
The feed to and fractions from the process:

| Component Weight Percent | Feed | Products | | | |
|---|---|---|---|---|---|
| | | Acetic Acid | Organic | Aqueous | Reboiler |
| Acetone | 0.24 | 0 | 1.47 | 0.91 | 0 |
| Methyl Acetate | 2.37 | 0 | 17.67 | 4.63 | 0 |
| Ethyl Acetate | 1.92 | 0 | 24.26 | 3.26 | 0 |
| 2-Butanone | 1.95 | 0 | 17.37 | 4.64 | 0 |
| s-Butyl Acetate | 0.26 | 0 | 5.75 | 0.22 | 0 |
| n-Butyl Acetate | 0.04 | 0 | 0.90 | 0.11 | 0 |
| 3-Bromo-2-Butanone | 0.59 | 0 | 8.79 | 0.70 | 0 |
| Formic Acid | 0.67 | 1.01 | 0.73 | 0.61 | 0.45 |
| Water | 21.33 | 3.56 | 10.78 | 72.87 | 0.02 |
| Acetic Acid | 63.87 | 93.26 | 5.66 | 3.75 | 65.59 |
| Propionic Acid | 3.10 | 1.89 | 1.26 | 0.68 | 10.70 |
| n-Butyric Acid | 1.56 | 0.22 | 0.79 | 0.17 | 9.58 |
| Heavy By-Products | 1.07 | 0 | 3.29 | 1.17 | 6.48 |
| Ionic Bromine | 0.62 | 0 | 0.02 | 0.01 | 4.15 |
| Cobalt | 0.26 | 0 | 0.05 | 0.01 | 3.01 |
| Acetic Acid Recovered: 88.6% | | | | | |

EXAMPLE 12

In this example part of the aqueous product is recycled to the feed tray.

The operating conditions are:
Feed Rate: 12.6 grams per minute
Acetic Acid Product: 8.10 grams per minute
Organic Product: 0.88 grams per minute
Aqueous Product: 2.25 grams per minute
Reboiler Product: 1.54 grams per minute
Reboiler Temperature: 128.3° C.
Top Vapor Temperature: 98.9° C.
Feed Tray Temperature: 102.5° C.
Molar Ratio Aqueous Reflux to Feed: 3.73:1.0
Molar Ratio Acetic Acid Product to Feed: 0.479:1.0
The feed to and fractions from the process:

| Component Weight Percent | Feed | Products | | | |
|---|---|---|---|---|---|
| | | Acetic Acid | Organic | Aqueous | Reboiler |
| Acetone | 0.47 | 0 | 2.94 | 1.45 | 0 |
| Methyl Acetate | 1.83 | 0 | 17.65 | 5.90 | 0 |
| Ethyl Acetate | 1.18 | 0 | 15.61 | 4.15 | 0 |
| 2-Butanone | 1.71 | 0 | 16.67 | 5.47 | 0 |
| s-Butyl Acetate | 0.30 | 0 | 5.59 | 0.96 | 0 |
| n-Butyl Acetate | 0.05 | 0 | 1.02 | 0.18 | 0 |
| 3-Bromo-2-Butanone | 0.70 | 0 | 9.05 | 2.18 | 0.01 |
| Formic Acid | 0.13 | 0.29 | 0.49 | 0.31 | 0.25 |
| Water | 24.0 | 0.49 | 11.76 | 58.88 | 0.40 |
| Acetic Acid | 65.86 | 98.15 | 13.8 | 18.79 | 84.27 |
| Propionic Acid | 2.14 | 0.98 | 1.13 | 0.48 | 6.15 |
| n-Butyric Acid | 0.92 | 0.09 | 0.64 | 0.17 | 3.13 |
| Heavy By-Product | 0 | 0 | 3.21 | 0.99 | 3.16 |
| Ionic Bromine | 0.18 | 0 | 0 | 0.08 | 1.21 |
| Cobalt | 0.25 | 0.0 | 0.01 | 0.01 | 1.42 |
| Acetic Acid Recovered: 95.8% | | | | | |

In the foregoing examples the value shown for "Acetic Acid Recovered" is based on the actual weights of acetic acid contents in the feed and in the acetic acid product.

Examples 5 through 12 illustrate how acetic acid content of the acetic acid product can be increased by the point in the fractionation of introduction of the aqueous product as reflux liquid (to top tray or feed tray) and by increasing the ratio of such reflux to feed.

Examples 1 through 4 illustrate how to effect removal of 3-bromo-2-butanone using the organic product as reflux. In this case the co-removal of water depends more on position in the fractionation system the organic product is recycled as reflux than on the reflux ratio, that is, the ratio of organic product to feed for this less energy demanding fractional distillation.

The following Comparative Example and Example 13 establish the criticality of the lower 68° C. top vapor temperature. In both examples the organic product is recycled.

EXAMPLE 13

The operating conditions are:
Feed Rate: 33.87 grams per minute
Acetic Acid Product: 28.7 grams per minute
Organic Product: 1.86 grams per minute
Aqueous Product: 0.51 grams per minute
Reboiler Product: 3.50 grams per minute
Reboiler Temperature: 126.7° C.
Top Vapor Temperature: 68.9° C.
Feed Tray Temperature: 91.7° C.
Acetic Acid Product Temperature: 98.3° C.
Molar Ratio Organic Product to Feed: 0.035:1
Molar Ratio Acetic Acid Product to Feed: 0.877:1.0
Molar Ratio Organic Reflux to Feed: 0.392:1.0
The feed to and fractions from the process:

| Component Weight Percent | Feed | Products Acetic Acid | Organic | Aqueous | Reboiler |
|---|---|---|---|---|---|
| Acetone | 0.20 | 0 | 2.76 | 3.16 | 0 |
| Methyl Acetate | 2.23 | 0 | 33.17 | 6.67 | 0 |
| Ethyl Acetate | 1.27 | 0 | 22.30 | 2.70 | 0 |
| 2-Butanone | 1.13 | 0.02 | 18.14 | 4.58 | 0 |
| s-Butyl Acetate | 0.29 | 0.01 | 5.19 | 0.21 | 0 |
| n-Butyl Acetate | 0 | 0 | 0.09 | 0.11 | 0 |
| 3-Bromo-2-Butanone | 0.59 | 0.42 | 2.11 | 0.37 | 0 |
| Formic Acid | 0.50 | 0.57 | 1.40 | 0.86 | 0.49 |
| Water | 21.7 | 24.50 | 7.37 | 74.21 | 0.23 |
| Acetic Acid | 68.76 | 73.08 | 5.11 | 5.61 | 77.53 |
| Propionic Acid | 1.22 | 1.04 | 0 | 0.08 | 4.44 |
| n-Butyric Acid | 0.45 | 0.15 | 0 | 0.1 | 2.86 |
| Heavy By-Products | 0.87 | 0.21 | 1.45 | 1.44 | 6.18 |
| Ionic Bromine | 0.40 | 0 | 0 | 0 | 4.78 |
| Cobalt | 0.29 | 0 | 0 | 0 | 3.19 |
| Acetic Acid Recovered: 90% | | | | | |

Although the 3-bromo-2-butanone removal was not as good as in previous illustrative processes it is more than twice as efficient as is accomplished in the Comparative Example.

COMPARATIVE EXAMPLE

The operating conditions are:
Feed Rate: 32.81 grams per minute
Acetic Acid Product: 27.52 grams per minute
Organic Product: 2.06 grams per minute
Aqueous Product: 0
Reboiler Product: 3.15 grams per minute
Reboiler Temperature: 126° C.
Top Vapor Temperature: 67.2° C.
Feed Tray Temperature: 101.7° C.
Acetic Acid Product Temperature: 98.9° C.
Molar Ratio Organic Product to Feed: 0.041:1.0
Molar Ratio Acetic Acid Product to Feed: 0.911:1.0
Molar Ratio Organic Reflux to Feed: 0.409:1.0
The feed to and fractions from the process:

| Component Weight Percent | Feed | Products Acetic Acid | Organic | Aqueous | Reboiler |
|---|---|---|---|---|---|
| Acetone | 0.18 | 0 | 2.93 | | 0 |
| Methyl Acetate | 2.60 | 0 | 36.06 | | 0 |

-continued

| Component Weight Percent | Feed | Products Acetic Acid | Organic | Aqueous | Reboiler |
|---|---|---|---|---|---|
| Ethyl Acetate | 1.41 | 0 | 23.90 | | 0 |
| 2-Butanone | 1.15 | 0 | 0.65 | | 0 |
| s-Butyl Acetate | 0.31 | 0.01 | 5.19 | | 0 |
| n-Butyl Acetate | 0.09 | 0 | 0.04 | | 0 |
| 3-Bromo-2-Butanone | 0.53 | 0.86 | 0.43 | | 0 |
| Formic Acid | 0.65 | 0.68 | 1.36 | | 0.55 |
| Water | 21.80 | 26.30 | 7.64 | | 0.26 |
| Acetic Acid | 67.48 | 70.57 | 1.36 | | 77.09 |
| Propionic Acid | 1.43 | 1.17 | 0 | | 5.37 |
| n-Butyric Acid | 0.50 | 0.19 | 0 | | 3.26 |
| Heavy By-Products | 1.10 | 0.20 | 2.15 | | 6.94 |
| Ionic Bromine | 0.40 | 0 | 0 | | 3.93 |
| Cobalt | 0.29 | 0 | 0 | | 2.61 |
| Acetic Acid Recovered: 87.7% | | | | | |

In the foregoing two examples the same apparatus was used as was used and described with respect to Examples 1 through 12.

EXAMPLE 14

Operating Conditions: Total reflux of aqueous product to top tray.
Acetic Acid Product: 22.7 grams per minute
Organic Product: 2.6 grams per minute
Reboiler Product: 5.8 grams per minute
Reboiler Temperature: 122.1° C.
Top Vapor Temperature: 97.2° C.
Feed Tray Temperature: 102.8° C.
Acetic Acid Product Temperature: 108.3° C.
Molar Ratio Organic Product to Feed: 0.064:1
Molar Ratio Acetic Acid Product to Feed: 0.824:1
Weight Ratio Reflux to Feed: 0.80:1

| Components, Weight Percent | Feed | Product Organic | Aqueous | Reboiler | Acetic Acid |
|---|---|---|---|---|---|
| Butane | 0.08 | 0.59 | 0.00 | 0.00 | 0.00 |
| Acetone | 0.35 | 3.71 | 0.00 | 0.00 | 0.00 |
| Methyl Acetate | 1.89 | 24.47 | 0.00 | 0.00 | 0.00 |
| Ethyl Acetate | 1.34 | 18.93 | 0.00 | 0.00 | 0.00 |
| 2-Butanone | 1.09 | 15.10 | 0.00 | 0.00 | 0.01 |
| S—Butyl Acetate | 0.33 | 4.73 | 0.00 | 0.01 | 0.01 |
| N—Butyl Acetate | 0.00 | 0.00 | 0.00 | 0.00 | 0.00 |
| 3-Br—2-Butanone | 0.62 | 8.78 | 0.00 | 0.05 | 0.00 |
| Formic Acid | 0.69 | 0.38 | 0.00 | 0.34 | 0.72 |
| Water | 19.60 | 13.99 | 0.00 | 0.04 | 26.60 |
| Acetic Acid | 70.94 | 6.24 | 0.00 | 87.18 | 71.89 |
| Propionic Acid | 1.23 | 0.68 | 0.00 | 4.05 | 0.67 |
| I—Butyric Acid | 0.00 | 0.00 | 0.00 | 0.00 | 0.00 |
| N—Butyric Acid | 0.41 | 0.30 | 0.00 | 1.80 | 0.08 |
| Unknowns | 0.80 | 2.10 | 0.00 | 3.09 | 0.02 |
| Ionic Bromine | 0.35 | 0.00 | 0.00 | 1.92 | 0.00 |
| Cobalt | 0.27 | 0.00 | 0.00 | 1.47 | 0.00 |

EXAMPLE 15

Operating Conditions: Part of the aqueous product is refluxed to the top tray and part to the feed tray.
Acetic Acid Product: 23.7 grams per minute
Organic Product: 2.5 grams per minute
Reboiler Product: 4.9 grams per minute
Reboiler Temperature: 122.2° C.
Top Vapor Temperature: 96.7° C.
Feed Tray Temperature: 102.2° C.
Acetic Acid Product Temperature: 107.7° C.
Molar Ratio Organic Product to Feed: 0.057:1
Molar Ratio Acetic Acid Product to Feed: 0.68:1

Weight Ratio Top Tray Reflux to Feed: 0.604:1
Weight Ratio of Reflux to feed tray to feed: 0.211:1

| Components, Weight Percent | Feed | Product Organic | Aqueous | Reboiler | Acetic Acid |
|---|---|---|---|---|---|
| Butane | 0.12 | 0.88 | 0.00 | 0.00 | 0.02 |
| Acetone | 0.58 | 3.63 | 0.00 | 0.00 | 0.00 |
| Methyl Acetate | 2.63 | 24.81 | 0.00 | 0.00 | 0.00 |
| Ethyl Acetate | 1.67 | 20.07 | 0.00 | 0.00 | 0.00 |
| 2-Butanone | 1.54 | 14.62 | 0.00 | 0.00 | 0.00 |
| S—Butyl Acetate | 0.15 | 5.46 | 0.00 | 0.00 | 0.00 |
| N—Butyl Acetate | 0.00 | 0.00 | 0.00 | 0.00 | 0.00 |
| 3-Br—2-Butanone | 0.67 | 8.26 | 0.00 | 0.30 | 0.50 |
| Formic Acid | 0.61 | 0.51 | 0.00 | 0.38 | 1.02 |
| Water | 23.40 | 17.81 | 0.00 | 0.08 | 15.40 |
| Acetic Acid | 65.42 | 5.45 | 0.00 | 85.14 | 81.97 |
| Propionic Acid | 1.22 | 0.58 | 0.00 | 4.58 | 0.77 |
| I—Butyric Acid | 0.00 | 0.00 | 0.00 | 0.00 | 0.00 |
| N—Butyric Acid | 0.42 | 0.21 | 0.00 | 2.06 | 0.08 |
| Unknowns | 0.98 | 2.70 | 0.00 | 3.50 | 0.24 |
| Ionic Bromine | 0.33 | 0.00 | 0.00 | 2.23 | 0.00 |
| Cobalt | 0.26 | 0.00 | 0.00 | 1.73 | 0.00 |

EXAMPLE 16

Operating Conditions: Part of the organic product is refluxed to the top tray and all of the aqueous product is refluxed to the feed tray.
Acetic Acid Product: 23.82 grams per minute
Organic Product: 2.21 grams per minute
Reboiler Product: 2.45 grams per minute
Reboiler Temperature: 125.6° C.
Top Vapor Temperature: 82.2° C.
Feed Tray Temperature: 102.5° C.
Acetic Acid Product Temperature: 108.3° C.
Molar Ratio Organic Product to Feed: 0.052:1
Molar Ratio Acetic Acid Product to Feed: 0.811:1
Weight Ratio Organic Reflux to Feed: 0.683:1
Weight Ratio Aqueous Reflux to feed: 0.053:1

| Components, Weight Percent | Feed | Product Organic | Aqueous | Reboiler | Acetic Acid |
|---|---|---|---|---|---|
| Butane | 0.08 | 0.37 | 0.00 | 0.00 | 0.01 |
| Acetone | 0.42 | 3.40 | 0.00 | 0.00 | 0.00 |
| Methyl Acetate | 2.23 | 24.44 | 0.00 | 0.00 | 0.00 |
| Ethyl Acetate | 1.54 | 23.88 | 0.00 | 0.00 | 0.00 |
| 2-Butanone | 1.28 | 18.56 | 0.00 | 0.00 | 0.00 |
| S—Butyl Acetate | 0.37 | 5.10 | 0.00 | 0.00 | 0.00 |
| N—Butyl Acetate | 0.10 | 0.51 | 0.00 | 0.00 | 0.01 |
| 3-Br-2-Butanone | 0.65 | 5.26 | 0.00 | 0.09 | 0.04 |
| Formic Acid | 0.72 | 0.29 | 0.00 | 0.53 | 0.86 |
| Water | 22.50 | 9.54 | 0.00 | 0.24 | 19.50 |
| Acetic Acid | 66.89 | 7.15 | 0.00 | 78.30 | 78.24 |
| Propionic Acid | 1.31 | 0.18 | 0.00 | 5.36 | 1.01 |
| I—Butyric Acid | 0.00 | 0.00 | 0.00 | 0.00 | 0.00 |
| N—Butyric Acid | 0.48 | 0.05 | 0.00 | 3.02 | 0.15 |
| Unknowns | 0.81 | 1.26 | 0.00 | 5.63 | 0.18 |
| Ionic Bromine | 0.38 | 0.00 | 0.00 | 4.07 | 0.00 |
| Cobalt | 0.24 | 0.00 | 0.00 | 2.75 | 0.00 |

EXAMPLE 17

Operating Conditions: Part of the organic product is refluxed to the top tray and all of the aqueous product is refluxed to the feed tray.
Acetic Acid Product: 22.17 grams per minute
Organic Product: 2.83 grams per minute
Reboiler Product: 5.14 grams per minute
Reboiler Temperature: 122.7° C.
Top Vapor Temperature: 83.3° C.
Feed Tray Temperature: 102.8° C.
Acetic Acid Product Temperature: 107.8° C.
Molar Ratio Organic Product to Feed: 0.069:1
Molar Ratio Acetic Acid Product to Feed: 0.796:1
Weight Ratio Organic Reflux to Feed: 0.840:1
Weight Ratio Aqueous Reflux to feed: 0.109:1

| Components, Weight Percent | Feed | Product Organic | Aqueous | Reboiler | Acetic Acid |
|---|---|---|---|---|---|
| Butane | 0.06 | 0.12 | 0.00 | 0.00 | 0.01 |
| Acetone | 0.42 | 3.94 | 0.00 | 0.00 | 0.00 |
| Methyl Acetate | 2.25 | 24.93 | 0.00 | 0.00 | 0.00 |
| Ethyl Acetate | 1.57 | 21.42 | 0.00 | 0.00 | 0.00 |
| 2-Butanone | 1.30 | 16.62 | 0.00 | 0.00 | 0.00 |
| S—Butyl Acetate | 0.36 | 5.15 | 0.00 | 0.00 | 0.00 |
| N—Butyl Acetate | 0.06 | 0.64 | 0.00 | 0.00 | 0.00 |
| 3-Br—2-Butanone | 0.60 | 8.11 | 0.00 | 0.08 | 0.01 |
| Formic Acid | 0.62 | 0.37 | 0.00 | 0.41 | 0.83 |
| Water | 19.43 | 11.86 | 0.00 | 0.39 | 23.26 |
| Acetic Acid | 69.70 | 4.49 | 0.00 | 85.17 | 74.87 |
| Propionic Acid | 1.33 | 0.31 | 0.00 | 4.25 | 0.84 |
| I—Butyric Acid | 0.00 | 0.00 | 0.00 | 0.00 | 0.00 |
| N—Butyric Acid | 0.47 | 0.07 | 0.00 | 2.02 | 0.11 |
| Unknowns | 1.19 | 1.96 | 0.00 | 3.43 | 0.05 |
| Ionic Bromine | 0.38 | 0.00 | 0.00 | 2.48 | 0.00 |
| Cobalt | 0.25 | 0.00 | 0.00 | 1.77 | 0.00 |

EXAMPLE 18

Operating Conditions: Part of the organic product is refluxed to the top tray and all of the aqueous product is refluxed to the top tray.
Acetic Acid Product: 21.8 grams per minute
Organic Product: 2.22 grams per minute
Reboiler Product: 7.06 grams per minute
Reboiler Temperature: 121.1° C.
Top Vapor Temperature: 80.6° C.
Feed Tray Temperature: 102.8° C.
Acetic Acid Product Temperature: 106.7° C.
Molar Ratio Organic Product to Feed: 0.048:1
Molar Ratio Acetic Acid Product to Feed: 0.789:1
Weight Ratio Organic Product Reflux to Feed: 0.630:1
Weight Ratio Aqueous Product Reflux to feed: 0.079:1

| Components, Weight Percent | Feed | Product Organic | Aqueous | Reboiler | Acetic Acid |
|---|---|---|---|---|---|
| Butane | 0.08 | 0.37 | 0.00 | 0.00 | 0.00 |
| Acetone | 0.44 | 4.71 | 0.00 | 0.00 | 0.00 |
| Methyl Acetate | 2.20 | 25.57 | 0.00 | 0.00 | 0.01 |
| Ethyl Acetate | 1.76 | 21.89 | 0.00 | 0.00 | 0.00 |
| 2-Butanone | 1.71 | 20.14 | 0.00 | 0.00 | 0.00 |
| S—Butyl Acetate | 0.45 | 5.80 | 0.00 | 0.00 | 0.00 |
| N—Butyl Acetate | 0.07 | 0.86 | 0.00 | 0.03 | 0.00 |
| 3-Br—2-Butanone | 0.44 | 5.67 | 0.00 | 0.08 | 0.00 |
| Formic Acid | 0.53 | 0.64 | 0.00 | 0.46 | 0.55 |
| Water | 19.80 | 8.33 | 0.00 | 0.37 | 26.40 |
| Acetic Acid | 69.25 | 3.78 | 0.00 | 88.08 | 72.03 |
| Propionic Acid | 1.28 | 0.17 | 0.00 | 3.33 | 0.79 |
| I—Butyric Acid | 0.00 | 0.00 | 0.00 | 0.00 | 0.00 |
| N—Butyric Acid | 0.52 | 0.08 | 0.00 | 1.76 | 0.14 |
| Unknowns | 0.78 | 1.99 | 0.00 | 2.46 | 0.08 |
| Ionic Bromine | 0.40 | 0.00 | 0.00 | 2.00 | 0.00 |
| Cobalt | 0.29 | 0.00 | 0.00 | 1.42 | 0.00 |

Those skilled in this art will from the foregoing illustrative examples of the conduct of the present inventive hetero-azeotropic fractional distillation, will be able to perceive other modes of operation within the scope of the present invention as defined by the appended claims.

The invention claimed is:

1. A fractional distillation method for removing bromo-organic compounds and water from an acetic acid-containing liquid oxidation effluent comprising the impurity 3-bromo-2-butanone, said effluent resulting from catalytic oxidation of liquid n-butane with oxygen gas in the presence of an acetic acid solution wherein the catalyst system comprises ions of bromine in combination with ions of cobalt or of manganese and cobalt followed by decompression of the acetic acid-containing liquid oxidation effluent to a gauge pressure of from about 3.5 up to about 21 kg/cm$^2$ to release unoxidized n-butane and coproduct gases therefrom said fractional distillation method comprising, in a fractionating system having a lower stripping zone, an upper rectification zone with a feed entrance between these zones, and a reboiling zone below the stripping zone the steps of:

separating 3-bromo-2-butanone present in the acetic acid-containing liquid oxidation effluent from the acetic acid present therein by fractionally distilling the effluent, which effluent includes essentially all of the 3-bromo-2-butanone impurity produced during the catalytic oxidation of liquid n-butane, to remove from the effluent a top fraction comprising a mixture including acetic acid, water, ketones, esters of acetic acid and 3-bromo-2-butanone, such mixture boiling at a temperature below the boiling temperature of acetic acid, said top fraction removal being accomplished by operating the rectification zone at a top gauge pressure of about 0 kg/cm$^2$ to provide a top vapor product comprising 3-bromo-2-butanone and having a temperature below about 100° C. but above about 68° C.; and cooling the vapor product to condense a top liquid product;

collecting the resulting top liquid product and permitting it to settle into two immiscible layers, i.e., an upper layer of organic product and a lower layer of aqueous product; and recycling aqueous product to the fractionation system.

2. The method of claim 1 wherein acetic acid is withdrawn from the stripping zone of the fractionation system as a vapor product.

3. The method of claim 2 wherein aqueous product is recycled to the top of the rectification zone.

4. The method of claim 2 wherein aqueous product is recycled to the feed entrance between the rectification and stripping zones.

5. A fractional distillation method for removing bromo-organic compounds and water from an acetic acid-containing liquid oxidation effluent comprising the impurity 3-bromo-2-butanone, said effluent resulting from catalytic oxidation of liquid n-butane with oxygen gas in the presence of an acetic acid solution wherein the catalyst system comprises ions of bromine in combination with ions of cobalt or of manganese and cobalt, followed by decompression of the acetic acid-containing liquid oxidation effluent to a gauge pressure of from about 3.5 up to about 21 kg/cm$^2$ to release unoxidized n-butane and coproduct gases therefrom, said fractional distillation method comprising, in a fractionation system having a lower stripping zone, an upper rectification zone with a feed entrance between these zones, and a reboiling zone below the stripping zone the steps of:

separating the 3-bromo-2-butanone present in the acetic acid-containing liquid oxidation effluent from the acetic acid present therein by fractionally distilling the effluent, which effluent includes essentially all of the 3-bromo-2-butanone impurity produced during the catalytic oxidation of liquid n-butane, to remove from the residue a top fraction comprising a mixture including acetic acid, water, ketones, esters of acetic acid and 3-bromo-2-butanone, such mixture boiling at a temperature below the boiling temperature of acetic acid, said top fraction removal being accomplished by operating the rectification zone at a top gauge pressure of about 0 kg/cm$^2$ to provide a top vapor product comprising 3-bromo-2-butanone and having a temperature below about 100° C. but above about 68° C. and cooling the vapor product to condense a top liquid product;

collecting the resulting top liquid product and permitting it to settle into two immiscible layers, i.e., an upper layer of organic product and a lower layer of aqueous product; and recycling organic product to the fractionation system.

6. The method of claim 5 wherein acetic acid is withdrawn from the stripping zone of the fractionation system as a vapor product.

7. The method of claim 6 wherein organic product is recycled to the top of the rectification zone.

8. The method of claim 6 wherein organic product is recycled to the feed entrance between the stripping and rectification zone.

9. The method of claim 6 wherein organic product is recycled to the stripping zone between the feed entrance and the withdrawal of the acetic acid vapor product.

10. A fractional distillation method for removing bromo-organic compounds and water from an acetic acid-containing liquid oxidation effluent comprising the impurity 3-bromo-2-butanone, said effluent resulting from catalytic oxidation of liquid n-butane with oxygen gas in the presence of an acetic acid solution wherein the catalyst system comprises ions of bromine in combination with ions of cobalt or of manganese and cobalt, followed by decompression of the acetic acid-containing liquid oxidation effluent to a gauge pressure of from about 3.5 up to about 21 kg/cm$^2$ to release unoxidized n-butane and coproduct gases therefrom, said fractional distillation method comprising, in a fractionation system having a lower stripping zone, an upper rectification zone with a feed entrance between these zones, and a reboiling zone below the stripping zone, the steps of:

separating the 3-bromo-2-butanone present in the acetic acid-containing liquid oxidation effluent from the acetic acid present therein by fractionally distilling the effluent, which effluent includes essentially all of the 3-bromo-2-butanone impurity produced during the catalytic oxidation of liquid n-butane, to remove from the residue a top fraction comprising a mixture including acetic acid, water, ketones, esters of acetic acid and 3-bromo-2-butanone, such mixture boiling at a temperature below the boiling temperature of acetic acid, said top fraction removal being accomplished by operating the rectification zone at a top gauge pressure of about 0 kg/cm$^2$ to provide a top vapor product comprising 3-bromo-2-butanone and having a temperature below about 100° C. but above about 68°

C. and cooling the vapor product to condense a top liquid product;

collecting the resulting top liquid product and permitting it to settle into two immiscible layers, i.e., an upper layer of organic product and a lower layer of aqueous product;

withdrawing acetic acid as a vapor product from the stripping zone of the fractionation system; and recycling to the top of the rectification zone one portion of each of organic product and aqueous product, and recycling a second portion of each product to the stripping zone above a point on the stripping zone at which acetic acid vapor is being withdrawn.

* * * * *